United States Patent [19]

Frazin

[11] Patent Number: 5,038,789
[45] Date of Patent: Aug. 13, 1991

[54] METHOD AND DEVICE FOR DOPPLER-GUIDED RETROGRADE CATHETERIZATION

[76] Inventor: Leon J. Frazin, 2106 N. Dayton, Chicago, Ill. 60614

[21] Appl. No.: 413,953

[22] Filed: Sep. 28, 1989

[51] Int. Cl.⁵ .............................................. A61B 8/06
[52] U.S. Cl. .............................................. 128/662.06
[58] Field of Search ......... 128/662.06, 661.07–661.10; 604/53

[56] References Cited

U.S. PATENT DOCUMENTS

| | | | |
|---|---|---|---|
| 3,443,433 | 5/1969 | Liston et al. | 128/662.06 |
| 4,175,566 | 11/1979 | Millar | 128/692 |
| 4,237,729 | 12/1980 | McLeod et al. | 73/861.25 |
| 4,577,637 | 3/1986 | Mueller, Jr. | 128/658 |
| 4,637,401 | 1/1987 | Johnston | 128/713 X |
| 4,665,925 | 5/1987 | Millar | 128/662.06 |
| 4,674,336 | 6/1987 | Johnston | 73/861.25 |
| 4,771,782 | 9/1988 | Millar | 128/637 |
| 4,771,788 | 9/1988 | Millar | 128/661.09 |
| 4,920,967 | 5/1990 | Cottonaro et al. | 128/662.06 |
| 4,947,852 | 8/1990 | Nassi et al. | 128/662.06 |

*Primary Examiner*—Francis Jaworski
*Attorney, Agent, or Firm*—Welsh & Katz, Ltd.

[57] ABSTRACT

A method is claimed for the intravascular catheterization of a higher mammal without fluoroscopy, which comprises inserting into a peripheral blood vessel a steerable catheter which has a Doppler ultrasound transceiver at its tip, generating from signals produced by the ultrasound transceiver a continuous indication of the direction of blood flow direction relative to the catheter tip, visually displaying the indication on a display monitor, and advancing the catheter towards the heart in accordance with the indication of blood flow direction until the catheter is positioned at a desired location within the circulatory system of the mammal.

A device for use in carrying out the inventive method is also claimed.

18 Claims, 1 Drawing Sheet

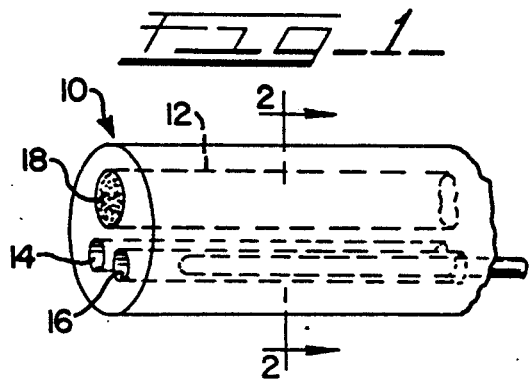
FIG_1
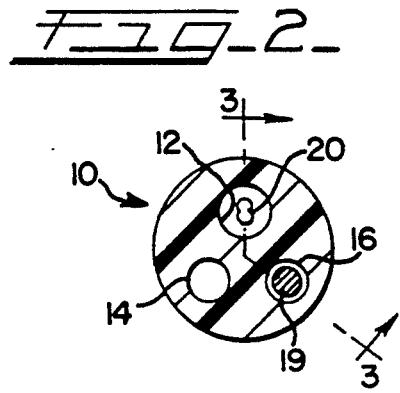
FIG_2
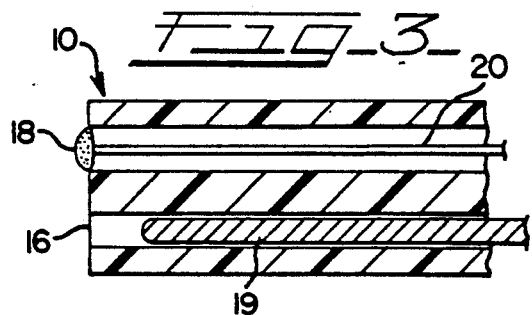
FIG_3
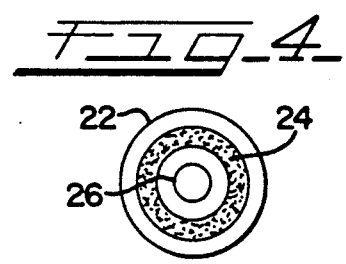
FIG_4
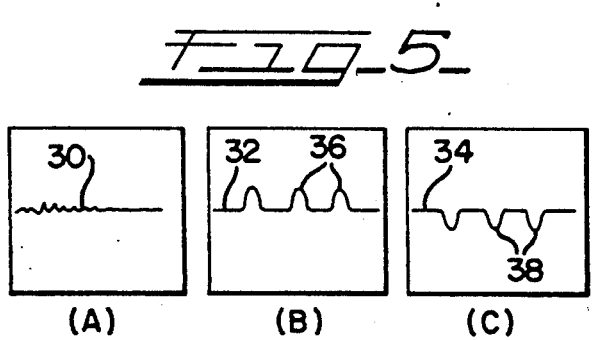
FIG_5
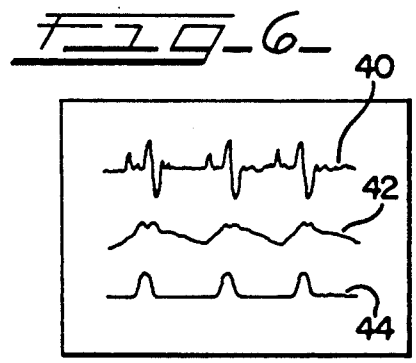
FIG_6
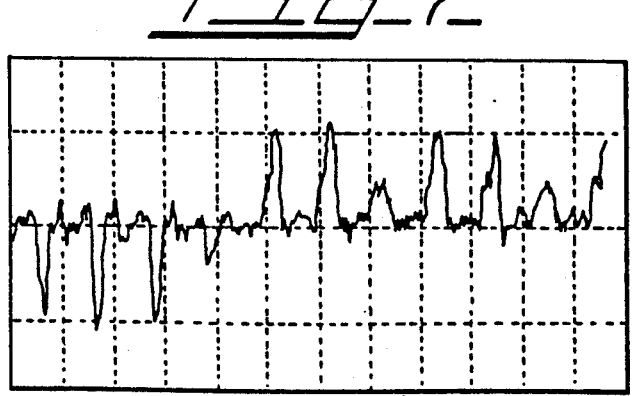
FIG_7

METHOD AND DEVICE FOR DOPPLER-GUIDED RETROGRADE CATHETERIZATION

BACKGROUND OF THE INVENTION

The present invention relates to a procedure for the intravascular catheterization of higher mammals, and in particular to a method and device for retrograde arterial catheterization without radiographic guidance. Specifically, the invention pertains to the use of a catheter-mounted Doppler ultrasound transceiver to selectively guide the catheter along the arterial tree towards the heart.

Vascular catheterization is practiced medically for a variety of reasons, and is used in both diagnostic and therapeutic procedures. In the case of radioangiography, for example, the catheter is used to deliver a radiopaque dye to a desired point in the circulatory system. The dye is then injected and is passively distributed while being visualized via fluoroscopy or radiography, providing an indication of blood flow and distribution. Alternatively, the catheter may carry a device for the treatment of intra-vascular defects, such as an inflatable balloon which can be used to enlarge an area of vascular constriction.

Diagnostic devices can be attached to such catheters so as to allow the taking of intravascular measurements. It has been suggested elsewhere to attach an ultrasonic transceiver to a vascular catheter, either at or near its tip. Patents issued to Liston et al. (U.S. Pat. No. 3,443,433), Millar (U.S. Pat. Nos. 4,175,566, 4,665,925, 4,771,782 and 4,771,788), McLeod et al. (U.S. Pat. No. 4,237,729), and Johnston (U.S. Pat. Nos. 4,637,401 and 4,674,336) reveal the use of ultrasonic transceivers in conjunction with arterial or venous catheters. In all of these references, however, the ultrasonic element is introduced to measure blood flow velocity only.

Moreover, these references teach only conventional methods of positioning a catheter. The placement of a catheter into or near the left heart has, until now, been accomplished by fluoroscopically monitoring the catheter's progress through the circulatory system. The reference of Johnston (U.S. Pat. No. 4,637,401) proposes inserting the catheter in a vein and allowing it to be pulled downstream to the site of interest; this technique is unsuitable, however, for reaching the left heart chambers and the blood vessels immediately downstream.

Catheterization of the left heart requires upstream or retrograde insertion of a catheter and has typically involved the use of fluoroscopic equipment, which is unavoidably bulky and expensive and therefore restricts the available locations in which catheterizations can be performed. A further drawback of fluoroscopy-guided catheterization arises when the catheter is insufficiently radiopaque, requiring the use of radiopaque indicators or plugs inserted at the catheter tip as suggested in U.S. Pat. No. 4,577,637. Yet another shortcoming is the undesirable exposure of the patient to radiation over long time periods, which necessarily occurs during fluoroscopy and which may pose a health risk as in the case of a pregnant patient.

SUMMARY OF THE INVENTION

It is therefore an object of the invention to overcome these and other difficulties associated with fluoroscopy-guided left heart catheterization. This object is attained by the method of the present invention, in which a catheter having a Doppler ultrasound transceiver at its tip is advanced while a continuous signal generated by the transceiver is monitored by the physician or technician. By observing signal characteristics which are indicative of blood flow direction, the operator is able to steer the catheter in the retrograde direction at each arterial branch, thereby eventually reaching the heart.

The inventive catheterization method has the advantage that no fluoroscopy or radiography is required to correctly position the catheter tip in or near the left heart. Instead of using a cumbersome fluoroscopic apparatus, the physician or cardiac catheterization technician can perform the procedure using a readily portable control device having an oscilloscope-type monitoring screen.

Another advantage of the inventive method is that catheters need not be modified or equipped with radiopaque elements to enhance their fluoroscopic visibility. Furthermore, the patient is not exposed to radiation during the procedure, allowing catheterizations to be performed on individuals for whom a fluoroscopically-guided catheterization is contraindicated.

These and other benefits of the present invention will be understood more clearly in connection with the following detailed description of the method of the invention.

BRIEF DESCRIPTION OF THE DRAWINGS

The invention is described with reference to several drawings, in which;

FIG. 1 is a perspective view of a multiple-lumen catheter suitable for use in the method of the present invention;

FIG. 2 is a cross-sectional view of the catheter of FIG. 1, taken along line 2—2 of FIG. 1;

FIG. 3 is a longitudinal section of the catheter of FIG. 1, taken along line 3—3 of FIG. 2;

FIG. 4 is an end view of an alternative catheter configuration;

FIGS. 5A-C are representative displays on a monitor used in the method of the present invention, showing tracings indicative of various positionings of the catheter tip;

FIG. 6 is a representative multi-functional display on a monitor used in the method of the present invention, and FIG. 7 is a representative monitor display used in the method of the present invention, showing tracings indicative of various positionings of the catheter tip as it advances through the femoral artery of a dog.

DETAILED DESCRIPTION OF THE INVENTION

The inventive method is herein described primarily in connection with catheterization of the left heart; however, it should be apparent that other procedures are likewise possible using Doppler-guided catheterization.

A steerable catheter 10 suitable for use in the method of the present invention is shown in FIGS. 1–3. Catheter 10 is a multiple-lumen catheter of well-known type, and has a first lumen 12 which is capped at its tip or distal end with a Doppler-type ultrasound transceiving crystal 18. Electrical leads 20 extend from the transceiver 18, through the length of lumen 12, to an external power supply and control apparatus. If desired, the electrical leads from crystal 18 can extend through two separated lumens, thereby eliminating the possibility of an electrical short circuit.

A second lumen 14 is hollow and at its proximal end is provided with a connector which allows the attachment of a variety of instruments, such as a manometric device for obtaining measurements of blood pressure at the catheter tip or a syringe for the injection of contrast media or therapeutic compounds. Lumen 14 may include two or more side holes near the tip for echo contrast injection. A third lumen 16 accommodates a guide wire 19 which may be of a J-tipped or other suitable type, with which the operator can steer the catheter during insertion.

Other catheter configurations may also be suitable for use with the method of the present invention. The above-described catheter 10 has a diameter of approximately 7–8 French (F), or approximately 2.5 mm. Narrower catheter diameters of 5–7 F are attainable by using a two-lumen catheter, in which a guide wire is fitted into the same lumen used for pressure measurement. A readily available Y-connector is then used at the proximal catheter port to allow both guide wire manipulation and pressure readings. Even narrower catheters may be used which have only one lumen. One such catheter 22 is shown in FIG. 4, and has a ring-shaped Doppler transceiver 24 surrounding a single lumen 26 which is used for both pressure measurement and a guide wire. In the case of catheter 22, the electrical leads attached to transceiver 24 may be embedded in the wall of the catheter.

The Doppler ultrasound control apparatus, which is connected to the transceiver 18 by leads 20, serves as a power supply for the transceiver which generates an ultrasound signal of approximately 20 megahertz. The apparatus also processes signals produced by the transceiver, and displays those signals as a tracing on an oscilloscope-type monitor.

The catheter is demarcated in centimeters to identify the distance from the arterial insertion site. The guide wire is also demarcated in centimeters to identify the distance that the end of the wire extends out of the catheter tip.

In the case of a cardiac catheterization performed according to the inventive method, the catheter 10 is inserted into the brachial or, preferably, the femoral artery using a suitable insertion sheath. The catheter is directed in the retrograde direction, i.e., against the flow of blood. This orientation of the catheter tip is indicated by a shift in the monitor display from the tracing 30 of FIG. 5A, which coincides with zero blood flow, to the tracing 32 of FIG. 5B. The appearance of upwardly-directed peaks 36 on the display is representative of blood flow towards the Doppler transceiver during systoly (i.e., contraction of the left ventricle). This is in contrast to the monitor display of FIG. 5C, in which blood flows away from the transceiver and produces systolic peaks 38 of tracing 34 which are directed downwardly.

The catheter 10 is next advanced through the arterial tree towards the heart while the monitor display is watched for any change in the tracing configuration. Should the operator accidentally guide the catheter into an incorrect arterial branch, the monitor tracing will show a downward deflection during systoly instead of an upward one, indicating that the direction of catheter advancement is no longer retrograde. The catheter is then withdrawn slightly, and rotated with possible guide wire adjustment. In this manner, the catheter is maneuvered into the correct vessel. Alternatively the catheter may be advanced without the use of a guide wire. The catheter may have sufficient rigidity and be of appropriate shape for some patients to permit advancement by manual force and slight periodic rotation.

The catheter is advanced until the aortic arch or a position superior to the aortic valve is reached. Guidance and positioning of the catheter are facilitated by monitoring the blood pressure at the catheter tip, using a manometric transducer connected to the open lumen 14. Advantageously, the output of this transducer as well as the patient's electrocardiograph (EKG) and the Doppler transceiver signal may be simultaneously displayed on a single monitor as shown in FIG. 6, in which tracings 40, 42, and 44 correspond to the EKG, pressure and Doppler ultrasound signals, respectively.

According to the present invention, the final positioning of the catheter tip can be accomplished by any of a number of non-fluoroscopic techniques. Guide wire manipulation may help crossing the aortic valve so as to enter the left ventricular chamber. The operator may be able to rely on pressure readings to establish that the left heart ventricle has been reached. Alternatively, a second ultrasound receiver may be used to receive the signal generated by the Doppler transceiver 18, and thus to accurately locate the catheter tip. Another possibility is that an external or esophageal ultrasound transceiver be used to observe the location of the metallic catheter tip within the heart.

Once the catheter has been properly placed, a variety of procedures may be carried out using the open catheter lumen 14 (as, for example, the measurement of left ventricular pressures or the injection of echogenic contrast materials for myocardial ultrasound perfusion analysis and valvicular regurgitation analysis). In other cases, such as where a different type of catheter is needed, the Doppler-guided catheter may be withdrawn while leaving the guide wire in place. The desired catheter is then inserted over the guide wire, and the guide wire withdrawn if necessary. In this fashion, the inventive method can be used to place any type of catheter in or near the heart.

The advantages of the present invention are further apparent in the case of a patient having a stenotic aortic valve. Cardiac catheterization is frequently difficult because of the partially occluded condition of such a valve. Using a Doppler-guided catheter, however, the operator is readily able to identify the exact location and timing of peak flow through even a badly stenosed valve, and to insert the catheter tip into the left heart. Likewise, the inventive method works well even in cases of arterial narrowing as by atherosclerosis, as the increased blood velocity through the affected vessel enhances the upward deflection of the ultrasound tracing.

The doppler wave form in the aorta could also be used to calculate stroke volume and therefore cardiac output (requires knowledge of aortic root diameter, which can be obtained with standard echocardiographic techniques).

Although the above description of the method of the present invention pertains to cardiac catheterization, it should be noted that Doppler-guided retrograde catheterization can be used equally well in studies of blood vessels or organs intermediate to the point of catheter insertion and the heart. For example, ultrasonic angiography of the iliac or renal arteries can be conducted by advancing the catheter tip just beyond the junction of the abdominal aorta and the artery in question. Using an external ultrasound transceiver to visualize the catheter or to receive signals from the catheter-mounted Doppler crystal, the catheter is positioned precisely and used to inject echogenic contrast material. Similarly, blood flow in the carotid arteries can be studied by choosing an appropriate injection point in the aortic arch. A further possible use of the invention is in venous anterograde catheterization, in which a Doppler-guided catheter is inserted in a suitable vein and advanced downstream towards the vena cava and right heart.

EXAMPLE 1

The method of the present invention was used in performing the Doppler-guided left heart catheterization of dogs.

A Doppler flow catheter was inserted into a 9 french guiding catheter which, in turn, was inserted through the femoral artery of the dog. The monitor display showed that the tracing on the left side of the graph (see FIG. 7) consisted of downwardly directed peaks below the base line which indicated that the blood flow was going toward the transducer, signifying that the guide catheter was being advanced in the correct direction. The right side of the graph of FIG. 7 showed upwardly directed peaks above the base line which indicated that the guide catheter had been inadvertently advanced into the wrong vessel.

FIG. 7 shows a tracing having downwardly directed peaks which indicates that the blood flow was going toward the transducer as compared to FIGS. 5 and 6 which show the inverse. This difference between FIGS. 5, 6, and FIG. 7 was due to a change in the polarity of equipment used in the respective tests.

Responsive to an abnormal tracing on the monitor display, as indicted in the above example, the catheter was slightly withdrawn from the artery, rotated and advanced in the direction where there was positive flow towards the transducer.

Following catheterization of the test animals, fluoroscopy was used to confirm that the catheter tip had been successfully positioned.

The above example and description of the inventive method are for the purpose of better illustrating its use, and are not intended to limit the scope of the invention. It will be appreciated by those familiar with the art that variations in the materials and techniques described herein are within the ambit of the claims which follow.

I claim:

1. A method for the intravascular catherization of a higher mammal without fluoroscopy, comprising:
   inserting into a peripheral blood vessel a catheter provided with an ultrasound transceiver, said catheter being inserted into the vessel and directed in the retrograde direction;
   generating from signals produced by the ultrasound transceiver a continuous indication of the direction of blood flow relative to the catheter;
   displaying said indication of blood flow direction; and
   advancing the catheter towards the heart in the retrograde direction in accordance with the indication of blood flow direction;
   whereby the catheter is selectively positioned at a desired location within the circulatory system of the mammal.

2. The method of claim 1 wherein the peripheral blood vessel is an artery.

3. The method of claim 2 wherein the artery is selected from the group consisting of the brachial and femoral arteries.

4. The method of claim 2 wherein the catheter is steerable.

5. The method of claim 4 wherein the catheter is steered with the use of a guide wire.

6. The method of claim 4 wherein the catheter is steered by rotation of the catheter.

7. The method of claim 6 wherein the catheter is advanced in accordance with the indications of both pressure and blood flow direction.

8. The method of claim 2 wherein the catheter is provided with means for obtaining indications of blood pressure within the artery.

9. The method of claim 8 wherein the means for obtainin pessure indications comprise a pressure transducer connected to the proximal end of a lumen extending through the catheter.

10. The method of claim 2 wherein the desired location at which the catheter is positioned is the aortic arch.

11. The method of claim 2 where in the desired location at which the catheter is positioned is superior to the aortic valve.

12. The method of claim 2 wherein the desired location at which the catheter is positioned is in the left ventricular chamber.

13. The method of claim 1 wherein the ultrasound transceiver is placed at the tip of the catheter.

14. A method for the catheterization of a human patient without fluoroscopy, comprising:
   inserting a catheter into a peripheral artery selected from the group consisting of the brachial and femoral arteries, the catheter having a Doppler ultrasound transceiver at its tip, at least one lumen capable of accommodating a guide wire, and at least one lumen capable of being connected to a pressure transducer, said catheter being inserted into the vessel and directed in the retrograde direction;
   generating from signals produced by the ultrasound transceiver a continuous indication of the direction of blood flow relative to the catheter tip;
   selectively connecting the pressure transducer to the catheter lumen and generating from signals produced by the pressure transducer an indication of blood pressure at the catheter tip;
   visually displaying the indications of pressure and blood flow direction; and
   advancing the catheter towards the heart in the retrograde direction in accordance with the indications of pressure and blood flow direction while rotating the catheter and selectively using the guide wire to steer the catheter;
   whereby the catheter tip is selectively positioned at a desired location within the circulatory system of the patient.

15. A device for the intravascular catheterization of a higher mammal without fluoroscopy, comprising:
   a catheter capable of insertion into a peripheral blood vessel;
   an ultrasound transceiver secured to the tip of the catheter, the transceiver being capable of producing an electrical signal indicative of the direction of blood flow relative to the catheter;
   a control unit capable of supplying power to the transceiver and of generating from the signal produced by the transceiver a continuous indication of blood flow direction;

wires connected to the transceiver, extending through the catheter from its tip towards its proximal end and connected to the control unit; and a display monitor visible to an operator of the device, the monitor being electrically connected to the control unit and capable of visually displaying the indication of blood flow direction;

whereby the operator if able, in accordance with the indication of blood flow direction, to advance and direct the catheter in the retrograde direction towards and selectively position the catheter in a desired location within the circulatory system of the mammal.

16. The device of claim 15 additionally comprising a pressure transducer in communication with a lumen of the catheter and capable of producing an electrical signal indicative of blood pressure at the catheter tip, the transducer being electrically connected to the control unit, the control unit being additionally capable of generating from the signal produced by the transducer an indication of blood pressure, and the display monitor being additionally capable of visually displaying the indication of blood pressure, whereby the operator is able to advance and position the catheter in accordance with the indications of both pressure and blood flow direction.

17. The device of claim 15 additionally comprising a guide wire inserted into a lumen of the catheter and capable of manipulation independently of the catheter, whereby the operator is able to steerably advance and position the catheter.

18. A method for the catheterization of a human patient without fluoroscopy, comprising:

inserting a catheter into a peripheral artery selected from the group consisting of the brachial and femoral arteries, the catheter having a Doppler ultrasound transceiver at its tip, at least one lumen extending the length of the catheter, said catheter being inserted into the vessel in the retrograde direction;

generating from signals produced by the ultrasound transceiver a continuous indication of the direction of blood flow relative to the catheter tip;

selectively connecting a pressure transducer to the catheter lumen and generating from signals produced by the pressure transducer an indication of blood pressure at the catheter tip;

visually displaying the indications of pressure and blood flow direction; and advancing the catheter towards the heart in the retrograde direction in accordance with the indications of pressure and blood flow direction while steering the catheter;

whereby the catheter tip is selectively positioned at a desired location within the circulatory system of the patient.

* * * * *

UNITED STATES PATENT AND TRADEMARK OFFICE
CERTIFICATE OF CORRECTION

PATENT NO. : 5,038,789

DATED : August 13, 1991

INVENTOR(S) : Leon J. Frazin

It is certified that error appears in the above-identified patent and that said Letters Patent is hereby corrected as shown below:

Column 6, line 17, delete "obtainin pressure" and insert --obtaining pressure--.

Signed and Sealed this

Nineteenth Day of January, 1993

*Attest:*

DOUGLAS B. COMER

*Attesting Officer*     *Acting Commissioner of Patents and Trademarks*